United States Patent
Draaijer et al.

(10) Patent No.: US 7,124,946 B2
(45) Date of Patent: Oct. 24, 2006

(54) OPTICAL READING DEVICE

(75) Inventors: Arie Draaijer, Zeist (NL); Robertus Cornelis Adrianus Onderwater, Ouderkerk aan de Amstel (NL)

(73) Assignee: Creative Research Solutions BVBA, Overijse (BE)

( * ) Notice: Subject to any disclaimer, the term of this patent is extended or adjusted under 35 U.S.C. 154(b) by 0 days.

(21) Appl. No.: 10/501,768

(22) PCT Filed: Jan. 17, 2003

(86) PCT No.: PCT/NL03/00038

§ 371 (c)(1),
(2), (4) Date: Jan. 10, 2005

(87) PCT Pub. No.: WO03/060494

PCT Pub. Date: Jul. 24, 2003

(65) Prior Publication Data

US 2005/0106067 A1    May 19, 2005

(30) Foreign Application Priority Data

Jan. 18, 2002  (NL)  .................................. 1019782

(51) Int. Cl.
*G06K 7/10* (2006.01)
(52) U.S. Cl. ..................................... 235/454
(58) Field of Classification Search ............... 235/454, 235/455, 459
See application file for complete search history.

(56) References Cited

U.S. PATENT DOCUMENTS

| | | | |
|---|---|---|---|
| 4,431,307 A | 2/1984 | Suovaniemi | |
| 4,810,096 A | 3/1989 | Russell et al. | |
| 5,307,144 A | 4/1994 | Hiroshi et al. | |
| 6,037,168 A * | 3/2000 | Brown | .................... 435/288.3 |
| 6,238,911 B1 * | 5/2001 | Kasahara | ................. 435/288.4 |
| 6,664,272 B1 * | 12/2003 | Snyder et al. | .............. 514/327 |

FOREIGN PATENT DOCUMENTS

| | | |
|---|---|---|
| EP | 0 640 828 | 3/1995 |
| EP | 0 697 460 | 2/1996 |
| WO | WO 82/000356 | 2/1982 |

* cited by examiner

*Primary Examiner*—Daniel Stoyr
(74) *Attorney, Agent, or Firm*—Young & Thompson

(57) ABSTRACT

An optical reading device comprising a housing for receiving a test plate on which, according to a fixed pattern, test substances can be provided, which reading device further comprises optical conversion elements for converting light coming from a test substance into a measuring signal which corresponds to a predetermined parameter of the test substance. The optical conversion elements comprise light-receiving areas configured in a pattern which corresponds to the pattern of the test plate. Due to the invention, it becomes possible to measure, in a non-invasive manner, an oxygen concentration in a test substance, such as a cell culture, without the oxygen content being disturbed by mechanical vibrations. As a result, in a reliable manner, measurements on substances can be performed for determining the toxicity and/or uptake or degradation rate in living cells.

10 Claims, 3 Drawing Sheets

OPTICAL READING DEVICE

This is a national stage of PCT/NL03/00038 filed Jan. 17, 2003 that claims priority of Netherlands Application No. 1019782 filed Jan. 18, 2002.

BACKGROUND OF THE INVENTION

The invention relates to an optical reading device, comprising a housing for receiving a test plate for testing test substances provided in a predetermined pattern on the test plate, and optical conversion elements for converting light, coming from the test substances, into a measuring signal which corresponds to a predetermined parameter of the test substances.

Such a reading device is known, for instance, from U.S. Pat. No. 4,810,096 and is used for determining absorption of light of test compounds which are received in a so-called microtitre plate, a transparent test plate manufactured from glass or a plastic and provided with a regular pattern of wells in which test substances can be provided, such as pharmacoactive substances or cell cultures.

A disadvantage of the known reading device is that it comprises moving parts, which have to be adjusted so that respective test positions in a microtitre plate can be read. This adjustment is complicated and can vary per plate or over time. Moreover, the mechanism is susceptible to maintenance. Further, the transport to the device, and its moving parts during testing, cause unnecessary disturbances in test substances, which is detrimental when it affects the test results if, for instance, the oxygen balances in the test substances are disturbed.

SUMMARY OF THE INVENTION

The object of the invention is to obviate the above-mentioned drawbacks and to provide an improved optical reading device, which renders it possible to test test substances provided on a test plate without disturbances.

This object is achieved in that the optical conversion elements comprise light-receiving areas, arranged in a plane according to a corresponding pattern to that of the test substances of the test plate.

Due to the invention, it is possible to provide an optical reading device without moving parts, so that testing is possible without the test being disturbed by measurements.

Preferably, the housing comprises a base plate, in which the optical conversion elements are included in a pattern which corresponds to the pattern of the test plate, which base plate has a form such that it can be coupled to a test plate for providing a direct, optical contact between the optical conversion elements and test substances on the test plate. The device can comprise coupling means for coupling the test plate to the base plate. This permits a compact arrangement while the signal yield is optimal. An alternative embodiment comprises a device wherein, with the aid of light conductors, such as, for instance, optical fibers, light is transported to an optically sensitive element.

Although other optical parameters can be detected too, such as color, absorption and transmission, the optically sensitive elements are preferably designed for registering light coming from a chemo-optical substance, for measuring a degree of concentration of a substance to which the chemo-optical substance is sensitive. In particular, the optical elements can register a half life of fluorescence light. Such fluorescence light can be emitted by an oxygen sensitive coating present at the testing positions of the test plate. Due to the invention, it becomes possible to measure, in a non-invasive manner, an oxygen concentration in a test substance, such as a cell culture. As a result, in a reliable manner, measurements can be performed on substances for determining the toxicity and/or uptake or degradation rate in living cells, which is of great importance in the current practice of so-called "high throughput" tests in the research of medicines.

Preferably, the optical reading device has a size which is only slightly larger than a standard microtitre plate, so that the reading device can be included and read in an incubator. As a result, it becomes possible to perform real-time measurements, without the conditions under which a cell culture takes place being altered. In a still further embodiment, the reading device comprises a light source for emitting excitation light, which light source emits light in a direction away from the light-receiving areas. Due to such a configuration, the reader can be designed as a compact part of the microtitre plate which can be coupled in a planar manner, so that this can be placed as a whole into the incubator.

The invention further relates to a method for testing test substances with an optical reader according to one of the preceding aspects, the method comprising the steps of providing the test substances in a microtitre plate, coupling the reader to the microtitre plate and inserting the reader into an incubator, while the measuring signals coming from the reader are stored in a memory in the reader and/or are outputted to a central processing unit.

The invention further relates to a microtitre plate provided with a chemo-optical coating. Preferably, the microtitre plate is provided with a gas tight closure for limiting the oxygen supply to a test substance. As a result, the vitality of a biological entity, such as, for instance, germinating seed, can be tested.

BRIEF DESCRIPTION OF THE DRAWINGS

Further advantages and features of the invention will be elucidated with reference to the drawing. In the drawing.

DESCRIPTION OF THE PREFERRED EMBODIMENTS

Figure 1:
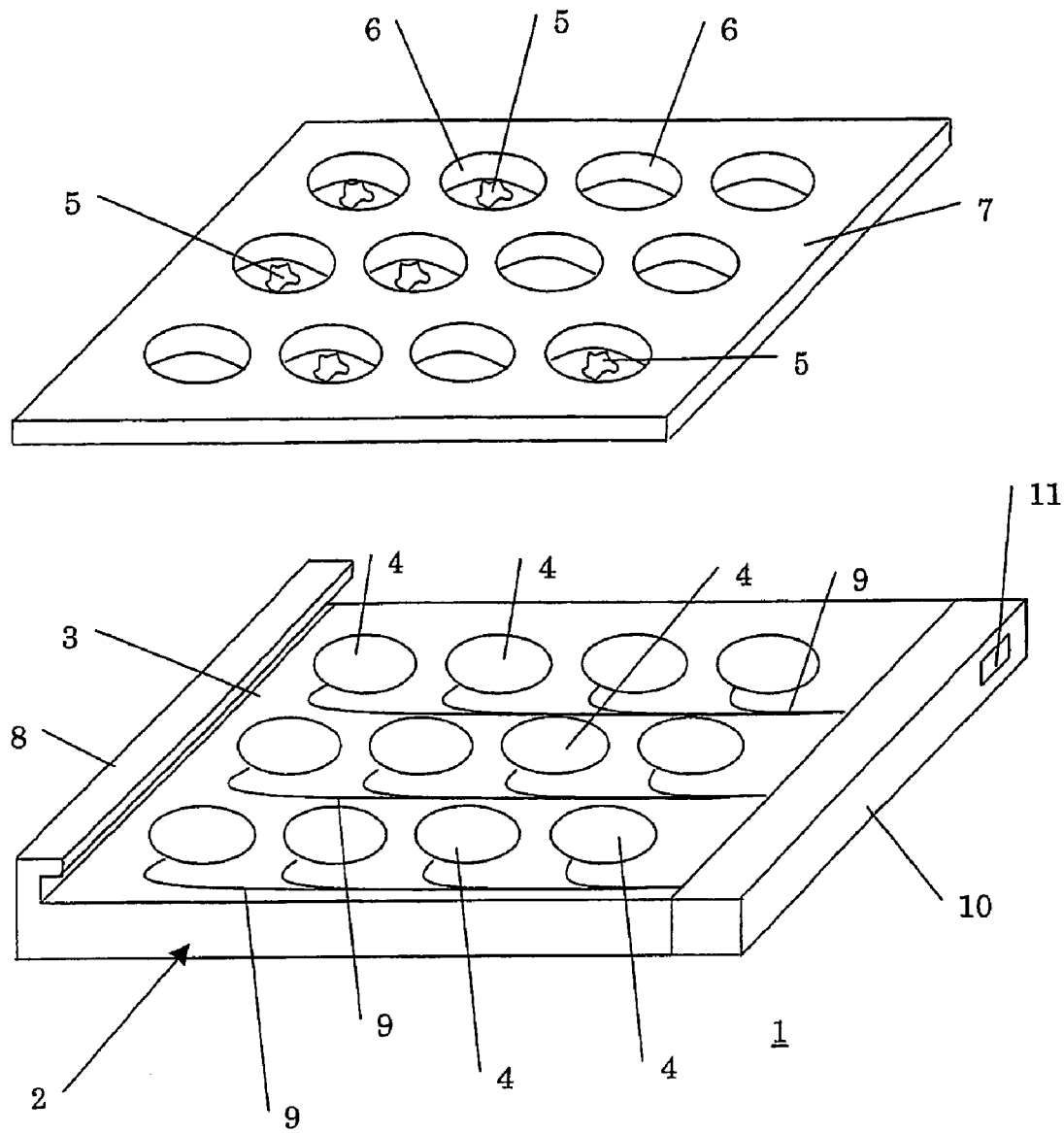
FIG. 1 shows a preferred embodiment of an optical reader according to the invention, in cooperation with a microtitre plate.

The optical reader 1 according to FIG. 1 comprises a housing 2 having a planar base plate 3, in which optical conversion elements 4 are received. The optical conversion elements 4 are, for instance, photodiodes, or a different type of semi-conductors which are sensitive to a relevant optical range. The optical converters 4 convert light which is emitted by test substances 5 provided in the wells 6 of a microtitre plate 7. The wells 6 of the microtitre plate 7 form a fixed pattern, in the example of the drawing a matrix-shaped pattern, of a number of wells which is common in practice, such as, for instance, a 96-well plate. In the drawing, for clarity's sake, only a limited number of wells are represented.

The conversion elements 4 have been provided in the base plate 3 in a similar type of pattern to the wells 6 of the microtitre plate 7, while the number of conversion elements is equal to the number of test positions of a-microtitre plate 7 to be read. In this manner, with the aid of one converter 4, each time, a test substance 5 of one test position can be analyzed, so that a mechanical movement of the converter to different positions, corresponding to different wells of the microtitre plate 7, is superfluous. The device according to the invention has a size which virtually corresponds to that of a standard microtitre plate, so that the reading device can be included in an incubator (not shown) for culturing biological material and can be read in situ, without mechanical disturbances occurring, in particular, without the plate having to be taken from the incubator. To that end, the invention comprises a method for testing test substances with an optical reader, the method comprising the steps of providing the test substances in a microtitre plate, coupling the reader to the microtitre plate and inserting the reader into an incubator, while the measuring signals coming from the reader are stored in a memory of the reader and/or are outputted to a central processing unit.

On the base plate 3, coupling elements 8 are present in the form of a groove, in which the test plate can be slid and fixed for forming a fixed connection with the optical reader 1.

Figure 2:
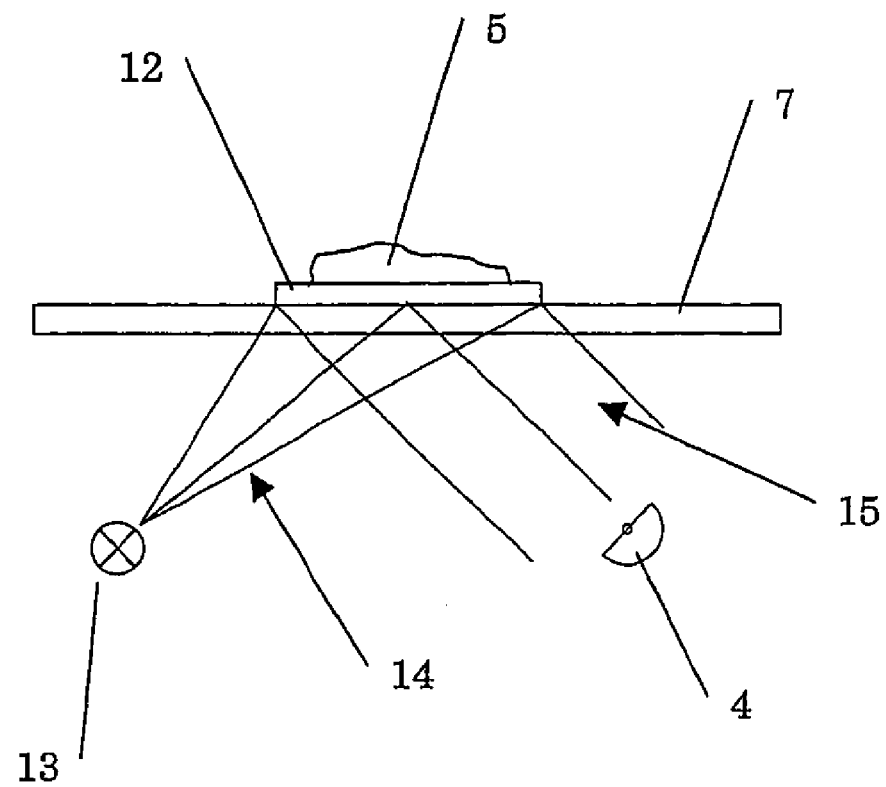
FIG. 2 shows a schematic representation of an optical reading with the optical reader according to the invention.

By means of connections 9, the converters 4 are connected to an electronic control unit 10, for controlling the respective converters 4, in particular for controlling the timing of the reading of the signals from a converter and/or the activation of a light source for exciting a chemo-optical compound (see FIG. 2). With the aid of an external coupling 11, the control unit 10 can be connected to a computer as peripheral equipment.

In FIG. 2, schematically, the operation of a preferred embodiment of the optical reader 1 is represented. The reader 1 is suited for analyzing light coming from a chemo-optical substance 12 which is brought into interaction with the test substance 5 in the microtitre plate 7, for determining the degree of concentration of a substance of interest in the test substance 5. To that end, in the optical reader, a light source 13 is included, emitting light 14 in a range to which the chemo-optical substance 12 is sensitive.

In the presence of the test substance 5, the chemo-optical substance 12 emits fluorescence light 15, which can be registered by a converter 4. From the signals of the converter 4, for instance through analysis of the total light yield or a half life of the intensity of the fluorescence light 15 emitted, the relevant degree of concentration can be determined. An example of this the measurement of the oxygen concentration in a test substance 7 with the aid of a fluorescence measurement on a ruthenium colorant or a different organo-metallic compound included in a gas-permeable matrix.

Figure 3:
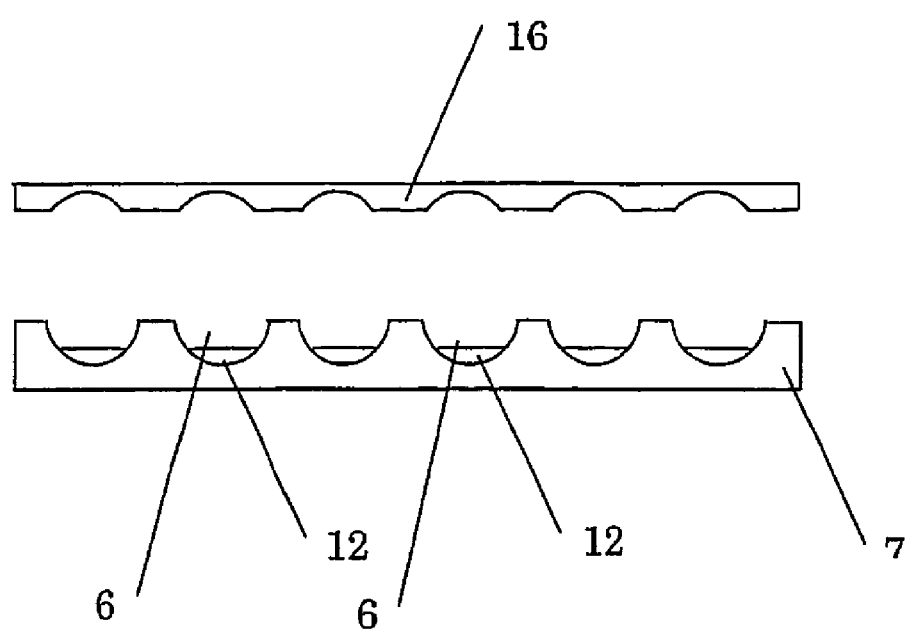
FIG. 3 shows a microtitre plate according to the invention.

In FIG. 3, schematically, a microtitre plate 7 according to the invention is represented. The microtitre plate 7 is a modified standard 96-well plate or comprises a different number of wells. The plate 7 comprises wells 6, in which a chemical substance or a particular biological material can be brought (not shown) for culturing and/or analysis. In the wells, a coating is provided, in which a chemo-optical material 12, such as the above-mentioned ruthenium complex, is included. In the example of the drawing, the microtitre plate 7 is further provided with a closure 16 which can be provided over the plate and, with the aid of glue or a different sealing means, can be closed off in a gas-tight, in particular oxygen-tight, manner. With the microtitre plate according to the invention, it is possible, in a non-invasive manner, to perform oxygen determinations on biological material, such as, for instance, seeds, so that its vitality can be analyzed.

Although the invention has been elucidated on the basis of the preferred embodiment, it is also possible to use different embodiments, which also fall within the scope of the claims. For instance, light conductors can then be used, which conduct the light of the light-receiving areas to a processing unit which can even be disposed outside an incubator, or otherwise. An excitation lamp can be centrally included in the reader, but also in a different manner, light can be supplied to a test substance to be analyzed. Apart from oxygen, also other chemical substances of interest, such as $CO_2$ or pH or other parameters of interest can be analyzed. Such variations are understood to fall within the scope of the invention as defined in the following claims.

The invention claimed is:

1. An optical reading device comprising:
    a housing for receiving a test plate on which, according to a fixed pattern, test substances can be provided; and
    optical conversion elements for converting light coming from a test substance into a measuring signal which corresponds to a predetermined parameter of the test substance,
    wherein the optical conversion elements comprise light-receiving areas configured in a pattern which corresponds to the pattern of the test plate,
    wherein the optically sensitive elements are designed for registering light coming from a chemo-optical substance, for measuring a degree of concentration of a substance to which the chemo-optical substance is sensitive, and
    wherein the optical elements register a half life of fluorescence light.

2. An optical reading device according to claim 1, characterized in that the housing comprises a base plate, in which the optical conversion elements have been received in a pattern which corresponds to the pattern of the test plate, which base plate has a shape such that the base plate can be coupled to a test plate for providing a direct optical contact between the optical conversion elements and test substances on the test plate.

3. An optical reading device according to claim 1, characterized in that the device comprises coupling means for coupling the test plate on the base plate.

4. An optical reading device according to claim 1, characterized in that the number of conversion elements is equal to the number of test positions of a test plate to be read.

5. An optical reading device according to claim 1, wherein the reading device has the size of a standard microtitre plate, so that the reading device can be included in an incubator and be read.

6. An optical reading device according to claim 1, characterized in that the reading device comprises a light source for- emitting excitation light, which light source emits light in a direction away from the light-receiving areas.

7. A method for testing test substances with an optical reader according to claim 1, characterized in that the method comprises the steps of providing the test substances in a microtitre plate, coupling the reader to the microtitre plate and inserting the reader into an incubator, while the measuring signals coming from the reader are stored in a memory of the reader and/or are outputted to a central processing unit.

8. A microtitre plate, characterized in that the microtitre plate is provided with coupling means for coupling the plate to an optical reader according to claim 1.

9. A microtitre plate according to claim 8, characterized in that the microtitre plate is provided with a chemo-optical coating.

10. A microtitre plate according to claim 9, characterized in that the coating is oxygen sensitive and that the microtitre plate comprises a closure for closing off the test substances in a gas-tight manner.

* * * * *